United States Patent
Ku et al.

(10) Patent No.: US 10,732,166 B2
(45) Date of Patent: Aug. 4, 2020

(54) METHOD FOR IN-LINE MEASUREMENT OF QUALITY OF MICROARRAY

(71) Applicant: Centrillion Technologies Taiwan Co. LTD., Hsinchu County (TW)

(72) Inventors: Tzu-Kun Ku, Hsinchu County (TW); Yao-Kuang Chung, Hsinchu County (TW); Yu-Chen Wang, Hsinchu County (TW); Po-Yen Liu, Hsinchu County (TW)

(73) Assignee: Centrillion Technologies Taiwan Co. LTD., Hsinchu County (TW)

( * ) Notice: Subject to any disclaimer, the term of this patent is extended or adjusted under 35 U.S.C. 154(b) by 80 days.

(21) Appl. No.: 15/896,079

(22) Filed: Feb. 14, 2018

(65) Prior Publication Data
US 2018/0238855 A1    Aug. 23, 2018

Related U.S. Application Data

(60) Provisional application No. 62/461,192, filed on Feb. 20, 2017.

(51) Int. Cl.
| | |
|---|---|
| *C12Q 1/68* | (2018.01) |
| *G01N 33/483* | (2006.01) |
| *G01Q 60/24* | (2010.01) |
| *G01Q 60/36* | (2010.01) |
| *G01Q 60/34* | (2010.01) |

(52) U.S. Cl.
CPC ......... *G01N 33/4833* (2013.01); *C12Q 1/68* (2013.01); *G01Q 60/24* (2013.01); *G01Q 60/34* (2013.01); *G01Q 60/363* (2013.01)

(58) Field of Classification Search
CPC .... C12Q 1/68; C12Q 2525/185; G01Q 60/24; G01Q 60/34; G01Q 60/363; G01N 33/4833
See application file for complete search history.

(56) References Cited

U.S. PATENT DOCUMENTS

| | | | |
|---|---|---|---|
| 8,666,471 B2 | 3/2014 | Rogers et al. | |
| 9,422,600 B2 | 8/2016 | Ramu et al. | |
| 2003/0134273 A1* | 7/2003 | Henderson | B82Y 35/00 435/5 |
| 2006/0246467 A1 | 11/2006 | Wade et al. | |
| 2009/0087346 A1 | 4/2009 | Luchini et al. | |

(Continued)

FOREIGN PATENT DOCUMENTS

| | | |
|---|---|---|
| CN | 1501085 | 6/2004 |
| CN | 101408496 | 8/2011 |

(Continued)

*Primary Examiner* — Betty J Forman
(74) *Attorney, Agent, or Firm* — JCIPRNET

(57) ABSTRACT

A method for in-line measurement of the quality of a microarray are disclosed and the method includes the following steps. A solid substrate is provided, and the solid substrate includes a plurality of areas in an array. At least one biomarker is in-situ synthesized on at least one of the plurality of areas by a plurality of synthesis steps. After performing at least one of the plurality of synthesis step, a check step is immediately performed on a semi-product of the at least one biomarker by an atomic force microscope to obtain an in-line measurement result. The quality of the semi-product of the at least one biomarker is determined based on the in-line measurement result.

18 Claims, 5 Drawing Sheets

(56) References Cited

U.S. PATENT DOCUMENTS

| | | | |
|---|---|---|---|
| 2009/0227040 A1* | 9/2009 | Sahin | B82Y 35/00 |
| | | | 436/94 |
| 2013/0309725 A1* | 11/2013 | Jacobson | C12N 15/1093 |
| | | | 435/91.5 |
| 2014/0308682 A1* | 10/2014 | Johnson, Jr. | G01N 33/54353 |
| | | | 435/7.8 |

FOREIGN PATENT DOCUMENTS

| | | |
|---|---|---|
| TW | I271517 | 1/2007 |
| TW | 201614075 | 4/2016 |

\* cited by examiner

METHOD FOR IN-LINE MEASUREMENT OF QUALITY OF MICROARRAY

CROSS-REFERENCE TO RELATED APPLICATION

This application claims the priority benefit of U.S. provisional application Ser. No. 62/461,192, filed on Feb. 20, 2017. The entirety of the above-mentioned patent application is hereby incorporated by reference herein and made a part of this specification.

BACKGROUND

Technical Field

The invention relates to a method for measurement of the quality of a microarray, in particular, to a method for in-line measurement of the quality of a microarray.

Description of Related Art

A microarray including synthesized biomarkers is widely used in the study of genetics, proteomics, pharmaceutical research and clinical detection. In order to obtain the detection results of the microarray with high accuracy and reliability, the quality of the microarray, that is, the quality of the synthesized biomarkers, is important.

Currently, the microarray is manufactured by immobilizing the synthesized biomarkers on a solid substrate in an array, and the quality of the synthesized biomarkers may be confirmed by fluorescence labeling and fluorescence detection. In other words, the quality of the microarray can be monitored only after the manufacture of the biomarkers has been completed. Therefore, providing a nondestructive method to timely ensure the quality of the biomarkers for the microarray is urgently required, especially for in-situ synthesized biomarkers.

SUMMARY

The present invention provides a method for in-line measurement of the quality of a microarray so that the microarray has the advantage of reduced cost and improved yield.

The present invention provides a method for in-line measurement of the quality of a microarray and includes the following steps. A solid substrate is provided, and the solid substrate includes a plurality of areas in an array. At least one biomarker is in-situ synthesized on at least one of the plurality of areas by a plurality of synthesis steps. After performing at least one of the plurality of synthesis step, a check step is immediately performed on a semi-product of the at least one biomarker by an atomic force microscope to obtain an in-line measurement result. The quality of the semi-product of the at least one biomarker is determined based on the in-line measurement result.

In an embodiment of the invention, the check step is performed once after performing one synthesis step.

In an embodiment of the invention, the check step is performed once after performing a predetermined number of synthesis steps.

In an embodiment of the invention, the solid substrate has a silanized surface, and the at least one biomarkers is synthesized on the silanized surface.

In an embodiment of the invention, the method further includes forming a quality monitor key on the solid substrate, and the quality monitor key is used as a control for the in-line measurement result.

In an embodiment of the invention, the method further includes forming an overlay mark on the solid substrate.

In an embodiment of the invention, the in-line measurement result includes at least one of height, surface morphology, surface defect, roughness, adhesion force, and density of the semi-product of the at least one biomarker.

In an embodiment of the invention, the in-line measurement result includes a ratio of adhesion force of the semi-product of the at least one biomarker to adhesion force of the solid substrate.

In an embodiment of the invention, the biomarker includes an oligonucleotide.

In an embodiment of the invention, the plurality of synthesis steps include a plurality of single nucleotide coupling steps.

In an embodiment of the invention, the plurality of synthesis steps further include a plurality of irradiating steps.

In an embodiment of the invention, one of the plurality of areas of the solid substrate has a size in the nano to micron range.

In an embodiment of the invention, one of the plurality of areas of the solid substrate has a size less than 100 micrometers.

In an embodiment of the invention, the at least one biomarker on one of the plurality of areas of the solid substrate includes at least one kind of biomarker.

In an embodiment of the invention, the method further includes checking a surface of the solid substrate by the atomic force microscope to obtain an initial measurement result before in-situ synthesizing at least one biomarker.

In an embodiment of the invention, the initial measurement result includes at least one of height, surface morphology, surface defect, roughness and adhesion force of the surface of the solid substrate.

In an embodiment of the invention, the surface of the solid substrate is a silanized surface.

In an embodiment of the invention, the method further includes comparing the initial measurement result and the in-line measurement result.

In an embodiment of the invention, the at least one biomarker is in-situ synthesized in multiple of the plurality of areas.

In an embodiment of the invention, the at least one biomarker is in-situ synthesized in multiple of the plurality of areas by the plurality of synthesis steps simultaneously.

Based on the above, the invention provides a method for in-line measurement of the quality of a microarray, which includes monitoring a semi-product of a biomarker (a semi-finished biomarker) synthesized in-situ by an atomic force microscope, and determining the quality of the semi-finished biomarker based on the in-line measurement result obtained from the atomic force microscope. Therefore, if the quality of the biomarker does not comply the requirements, which means the quality of the microarray does not comply the requirements, the manufacture of the microarray may be adjusted or stopped immediately. Accordingly, the cost of the microarray is reduced, and the accuracy, reliability and yield of the microarray are improved.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

The present invention provides a method for in-line measurement of the quality of a microarray. Since the quality of biomarkers is key for detection ability of the microarray, the quality of the microarray can be determined by measuring the quality of the biomarkers. The term "in-line measurement" means measurements in the measurement process (line) are included in the line.

Figure 1:
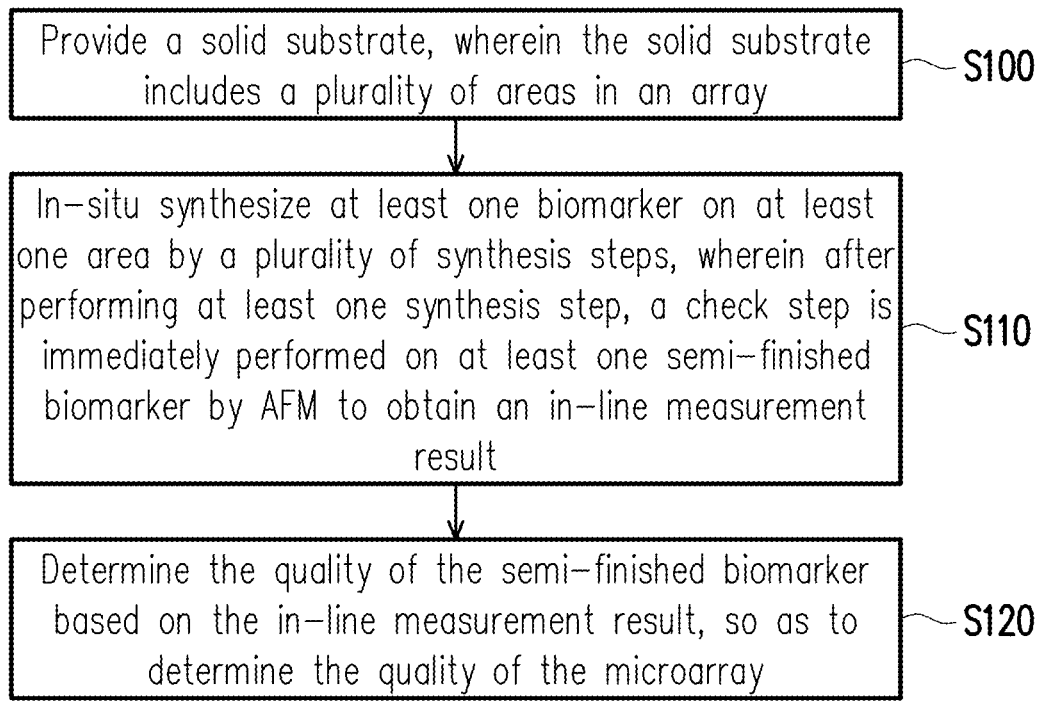
FIG. 1 illustrates a flowchart of a method for in-line measurement of the quality of a microarray according to some embodiments of the invention.

FIG. 1 illustrates a flowchart of a method for in-line measurement of the quality of a microarray according to some embodiments of the invention. Referring to FIG. 1, first, in step S100, a solid substrate is provided, and the solid substrate includes a plurality of areas in an array. In some embodiments, the solid substrate may be a wafer. A material of the wafer may be silicon, quartz or other suitable material, and the wafer may have a diameter of 2", 4", 6", 8", or 12", for example. In some embodiments, a surface of the solid substrate should be modified by a modifier, which may be selected from silanol, polylysine and alkoxysilane, for example. In some alternative embodiments, a silanization process may be performed on the surface of the solid substrate, and thus alkoxysilane is added on the surface of the solid substrate. Alkoxysilane includes aminosilane, glycidoxysilane and mercaptosilane, for example. After the silanization process, the solid substrate has a silanized surface for immobilizing the biomarkers. Besides silanization, the surface of the solid substrate can be modified with hydroxyl groups for sequential in-situ synthesis of the biomarker.

The areas are arranged in a plurality of columns and a plurality of rows. In some embodiments, the area of the solid substrate has a size, for example, in the nano to micron range. For example, the size of the area of the solid substrate is less than 100 microns, such as 500 nanometers to 100 micrometers or 1 micrometer to 100 micrometers. In some embodiments, the solid substrate further includes a quality monitor key thereon, and the quality monitor key is used as a control for the in-line measurement result. In addition, the quality monitor key can also contain an overlay mark thereon for misalignment measurement.

In step S110, at least one biomarker is in-situ synthesized on at least one area by a plurality of synthesis steps, and after performing at least one synthesis step, a check step is immediately performed on at least one semi-finished biomarker by an atomic force microscope (AFM) to obtain an in-line measurement result. In some embodiments, the solid substrate includes a plurality of areas, and each area has at least one biomarker synthesized thereon. In some embodiments, the biomarkers are synthesized in multiple of the areas. Therefore, a total number of the biomarkers may be larger than or equal to a total number of the areas, for example. The biomarkers may include ss-DNA, miRNA, aptamer, peptide, protein, antibody, fragments of antibody, or other suitable biomarker. Based on the sequence, the ss-DNA, miRNA, or aptamer is chemically synthesized using nucleotides (i.e., adenine, thymine, guanine, or cytosine) or nucleotide derivatives, and the peptide, protein, or antibody is chemically synthesized using amino acids (i.e., Ala, Arg, Asn, Asp, Cys, Glu, Gln, Gly, His, Ile, Leu, Lys, Met, Phe, Pro, Ser, Thr, Trp, Tyn, or Val). In some embodiments, the biomarkers have a length ranging from few angstroms to few nanometers. In some embodiments, the biomarkers have a length ranging from 20 mers to 50 mers.

In some embodiments, one biomarker may be synthesized by a synthesis process including a plurality of synthesis steps, that is, after performing all synthesis steps, one biomarker is formed completely. Therefore, during the synthesis process, that is, before finishing all synthesis steps, the biomarker is incomplete and referred to as a semi-finished biomarker. In some embodiments, the semi-finished biomarker includes at least two units such as two nucleotides, for example. In some embodiments, the biomarker includes an oligonucleotide, and the synthesis steps include a plurality of nucleotide coupling steps. In each nucleotide coupling step, one nucleotide is coupled to another nucleotide directly/indirectly connected to the solid substrate, and thus the oligonucleotide is elongated. In some embodiments, if the nucleotide has a photolabile protecting group, an irradiating step (a photo-exposure step) may be performed to remove the photolabile protecting group before the nucleotide coupling step. The synthesis process for the biomarker including a plurality of irradiating steps and nucleotide coupling steps may be also called a photosynthesis process. The biomarkers on different areas may be synthesized simultaneously or separately. The biomarkers on one area of the solid substrate include at least one kind of biomarker, that is, the biomarkers on one area may be the same or different. The biomarkers on different areas may be the same or different.

In some embodiments, the check step is performed once after performing one synthesis step to obtain an in-line measurement result. In other words, after one nucleotide is coupled to another nucleotide directly/indirectly connected to the solid substrate, at least one semi-finished biomarker is immediately observed by the atomic force microscope. In alternative embodiments, the check step is performed once after performing a predetermined number of synthesis steps, and a predetermined number is less than a total number of the synthesis steps and larger than 1. In alternative embodiments, the check step may be randomly performed during the synthesis process. In other words, the check step may be performed at any moment in the continuous synthesis process. Since the semi-finished biomarkers in different areas may be formed simultaneously by the same synthesis steps, the observation of at least one semi-finished biomarkers may represent the synthesis condition for all semi-finished biomarkers of the microarray. In some embodiments, according to the requirements, the check step may be performed on one semi-finished biomarker or multiple semi-finished biomarkers to confirm the quality of the microarray.

In some embodiments, the atomic force microscope includes a probe, a photoelectric detection system, an electronic control system, and a computer processing system, and the above systems are connected to one another by a circuit. The probe includes a microcantilever and a tip. The photoelectric detection system includes a laser light source and a photodetector. The laser light emitted by the laser light source shines on the back of the microcantilever. Since the back of the microcantilever is a mirror surface, the laser light is reflected on the back of the microcantilever and the reflected light is received by the photodetector. When the microcantilever is displaced, distorted or deformed by the atomic force on the surface of the biomarkers, the angle of incidence of the laser light emitted from the laser light source on the back of the microcantilever changes and correspondingly changes its reflection angle. The changes are received by the photodetector and converted into an electrical signal. The electrical signal is then input to the computer processing system to determine the amount of displacement, distortion or deformation of the microcantilever in a direction perpendicular to the surface of the biomarkers.

In some embodiments, the mode of scanning the biomarker by the probe includes, for example, a contact mode or a tapping mode. In the contact mode, the tip is in contact or near contact with the surface of the biomarker by small vertical force and large lateral force to drag the probe over the surface. In the tapping mode, the tip is intermittent contact by large vertical force and small lateral force. Additionally, the AFM can be operated in a variety of environments, including air or liquids.

Particularly, in some embodiments, the method of operating the AFM to observe the semi-finished biomarker includes the following steps. First, the microarray including the semi-finished biomarkers thereon is provided, and the semi-finished biomarkers have at least two nucleotides, for example. Then, the electronic control system of the AFM is used to control the probe to scan the surface of the microarray using the tapping mode. In some embodiments, a peak force tapping is used to measure the semi-finished biomarker under water or a buffer solution such as Tris buffer or phosphate buffered saline (PBS). In some embodiments, the peak force tapping applies, for example, 100~500 pN peak force to precisely control probe-to-oligonucleotide interaction and provides the highest resolution of AFM imaging, for example, sample line resolution with 256 or 512 pixels.

Furthermore, the probe displaces, distorts or deforms under the action of the probe contact with the surface of the semi-finished biomarker. The laser light emitted by the photoelectric detection system is used to detect the displacement, distortion or deformation of the probe generated on the vertical axis and producing an optical signal. The optical signal is converted into an electrical signal and then transmitting the electrical signal to the computer processing system. The computer processing system receives the electrical signal transmitted by the photoelectric detection system, analyzes and processes the displacement, distortion and deformation of the probe generated on the axis, so as to obtain the in-line measurement results. The in-line measurement results include at least one of height, surface morphology, surface defect, roughness, adhesion force, and density of the semi-finished biomarkers on the areas of the microarray.

In step S120, the quality of the semi-finished biomarker is determined based on the in-line measurement result, so as to determine the quality of the microarray. In some embodiments, the in-line measurement results such as height, surface morphology, surface defect, roughness, adhesion force, and density of the semi-finished biomarker on the area of the microarray is used to determine the quality of the microarray. For example, the completeness and distribution of the biomarkers of the microarray are determined based on the height and the surface morphology of the in-line measurement results. In some embodiments, the donut shape (which is a profile that an outer portion is higher than an inner portion in a region) or aggregated particles presented in the in-line measurement results means the biomarkers of the microarray has the surface defect and poor uniformity. In some embodiments, the height and the surface roughness of the in-line measurement results are used to determine the density of the biomarkers on the microarray. Additionally, in some embodiments, the quality of the solid substrate can be also checked by AFM before in-situ synthesizing the biomarker, to obtain an initial measurement result, which includes at least one of height, surface morphology, surface defect, roughness and adhesion force of the surface of the solid substrate. In some embodiments, the surface of the solid substrate is a silanized surface. In some embodiments, the method for in-line measurement of the quality of a microarray further includes the step of comparing the initial measurement result and the in-line measurement result.

In some embodiments, a ratio of adhesion force of the in-line measurement results may be used to determine the quality of the biomarkers on the microarray. Specifically, the ratio of adhesion force equals a ratio of adhesion force of the semi-product of the biomarker to adhesion force of the solid substrate, which means a value obtained by the adhesion force of biomarker divided by the adhesion force of (silanized) surface in the area. Once the ratio of adhesion force is close to 1, that is, the adhesion force of biomarker is similar to the adhesion force of (silanized) surface of the solid substrate, it means the quality of the biomarkers is poor. In other words, the adhesion ratio can also be an indicator for the quality of the biomarkers. In some embodiments, the area with the silanized surface may include an inner region where the biomarker is synthesized and an outer region where no biomarker is synthesized, and the ratio of adhesion force may be obtained by the adhesion force of the biomarker measured in the inner region divided by the adhesion force of the solid substrate measured in the outer region. In alternative embodiments, the adhesion force of silanized surface may be obtained by measuring the area before biomarker synthesis step, which is also the said initial measurement result. In some embodiments, the output of the microarray signal may be adjusted based on the in-line measurement result, and the software to control the manufacture of the microarray may apply the in-line measurement result as parameters to modify the result output. In other words, incorporation of the above steps into a manufacturing line enables automatic inspection of the micro array.

Briefly, in the method for in-line measurement of the quality of a microarray of present invention, the quality of the microarray is timely detected by in-situ observing the characteristics of the semi-finished biomarker by an atomic force microscope. In some embodiments, the semi-finished biomarker (the semi-finished microarray) can be constantly monitored. Therefore, if the quality of the microarray does not comply the requirements, the manufacture of the microarray may be adjusted or stopped immediately. Accordingly, the cost of the microarray is reduced, and the accuracy, reliability and yield of the microarray are improved. In addition, stable measurement can be repeated for large amounts of microarray products, and constant monitoring makes it possible to determine when unacceptable microarray products began to appear, which is helpful in managing traceability.

EXPERIMENTAL EXAMPLE

Example 1 as shown in table 1, using 250 pN peak force to measure the adhesion force of a biomarker and the adhesion force of a silanized surface in an area A or B. Then, the ratio of adhesion force is calculated by dividing the adhesion force of the biomarker by the adhesion force of the silanized surface in the area. In addition, a fluorescence intensity of the biomarker is measured by a fluorescence labeling or fluorescence detection method, which is used to determine the quality of the microarray conventionally.

TABLE 1 the adhesion force of the biomarker and the adhesion force of the silanized surface in different areas

| Area | Fluorescence intensity | Peak force applied (pN) | Ratio of adhesion force |
| --- | --- | --- | --- |
| A | <12000 | 250 | >0.5 |
| B | >15000 | 250 | <0.3 |

According to the results shown in table 1, comparing to the value of the ratio of adhesion force in area B, the value of the ratio of adhesion force in area A is closer to 1. It means the adhesion force of biomarker in area A is more similar to the adhesion force of silanized surface, and indicates poor quality of the biomarker in area A. The fluorescence intensity of the biomarker in area A is lower than that in area B, and it means the quality of the biomarker in area A is poorer than that in area B. Accordingly, the biomarker quality obtained by the ratio of adhesion force is consistent with the biomarker quality based on the fluorescence intensity. Therefore, the ratio of adhesion force can be an indicator for the biomarker quality.

Figure 2A:
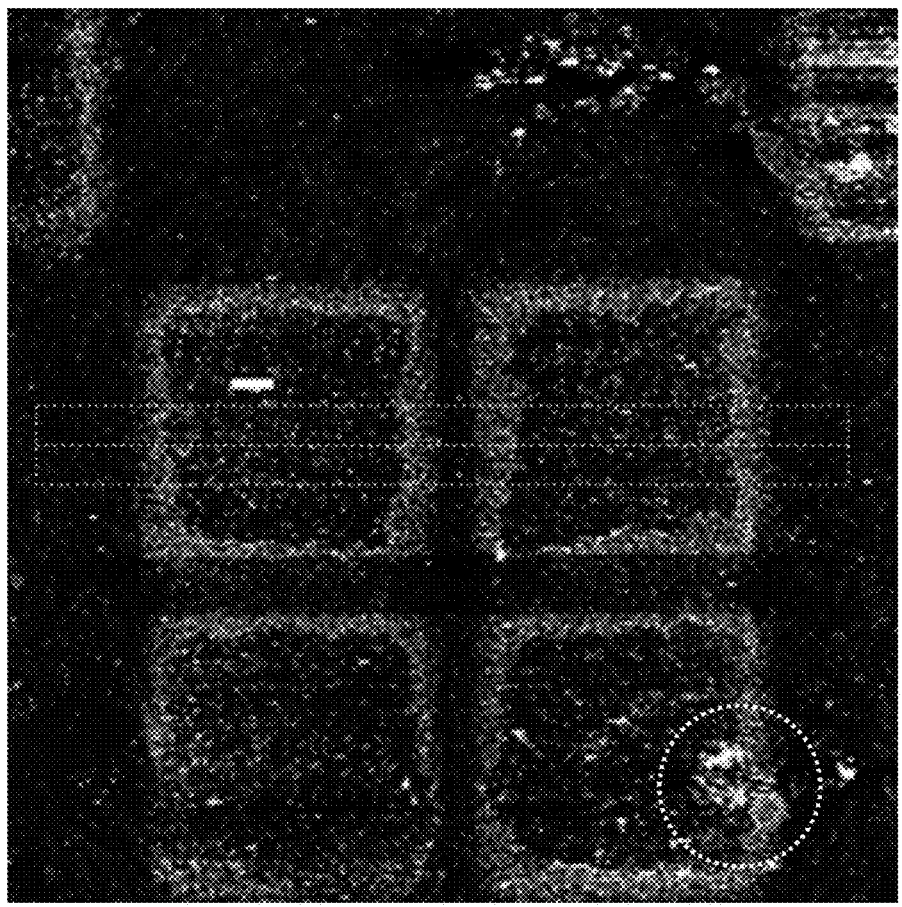
FIG. 2A is a schematic diagram of the in-line measurement results of the semi-finished biomarkers on a microarray in an experimental example of the present invention.
Figure 2B:
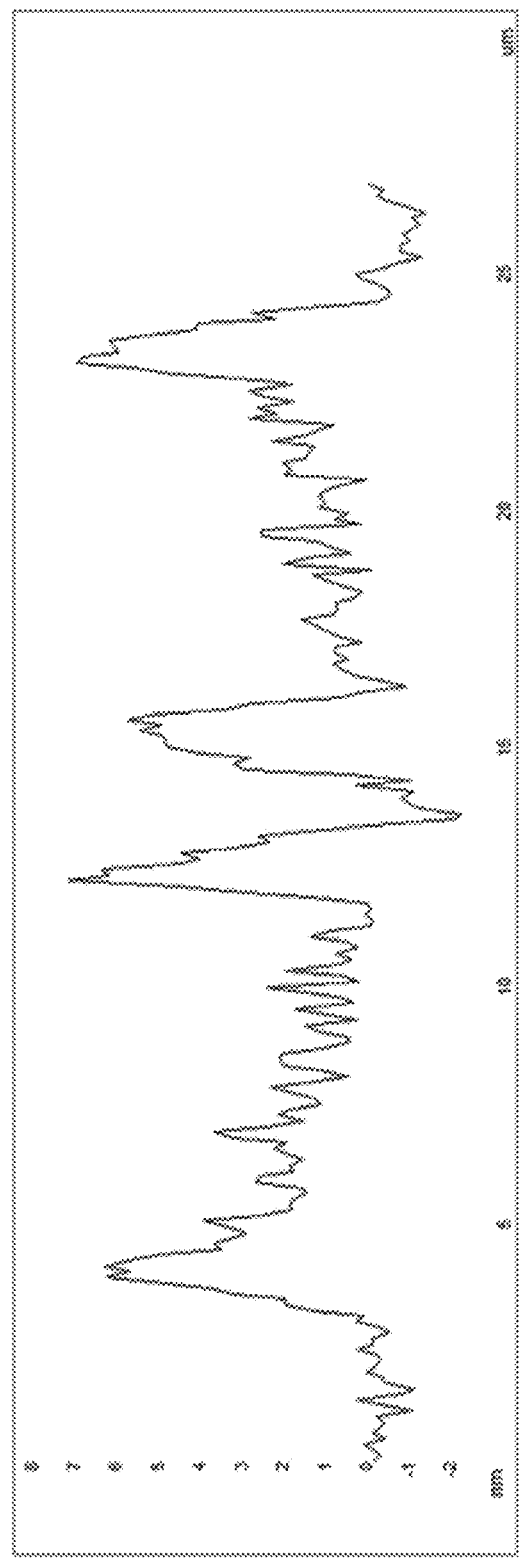
FIG. 2B is the in-line measurement results of mean height of the semi-finished biomarkers obtained from those in two regions (indicated by dashed boxes) of the microarray of FIG. 2A.
Figure 3A:
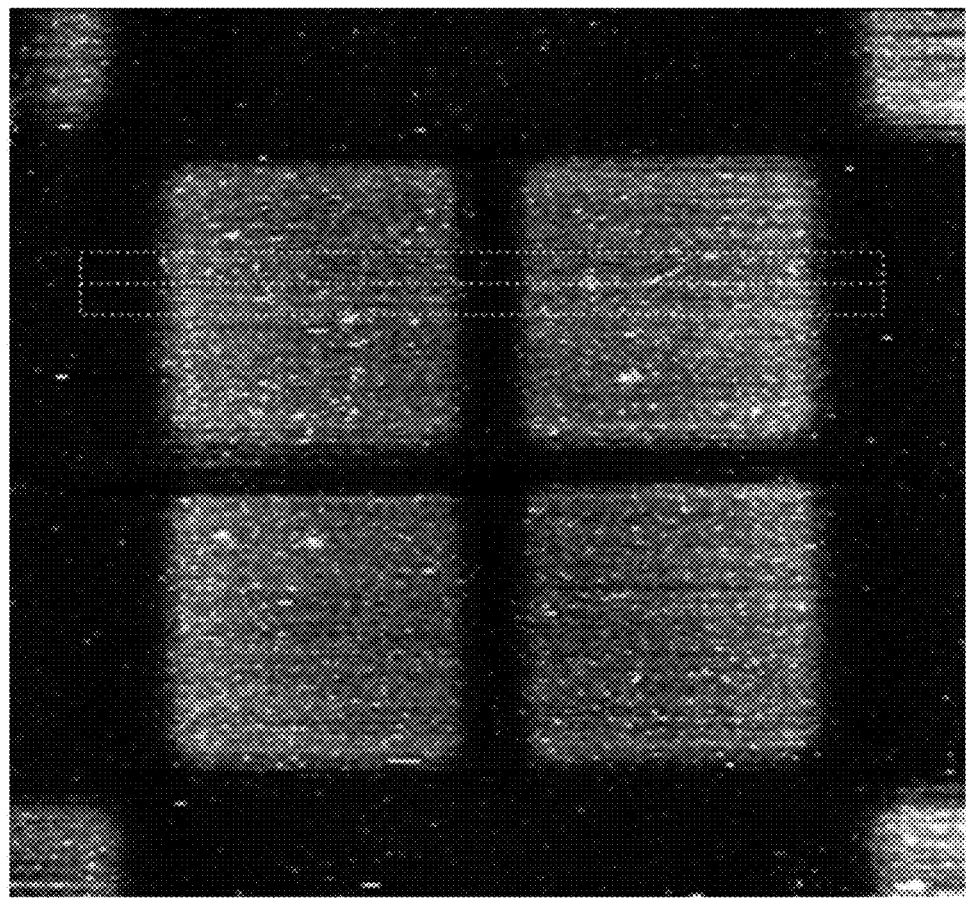
FIG. 3A is a schematic diagram of the in-line measurement results of the semi-finished biomarkers on a microarray in another experimental example of the present invention.
Figure 3B:
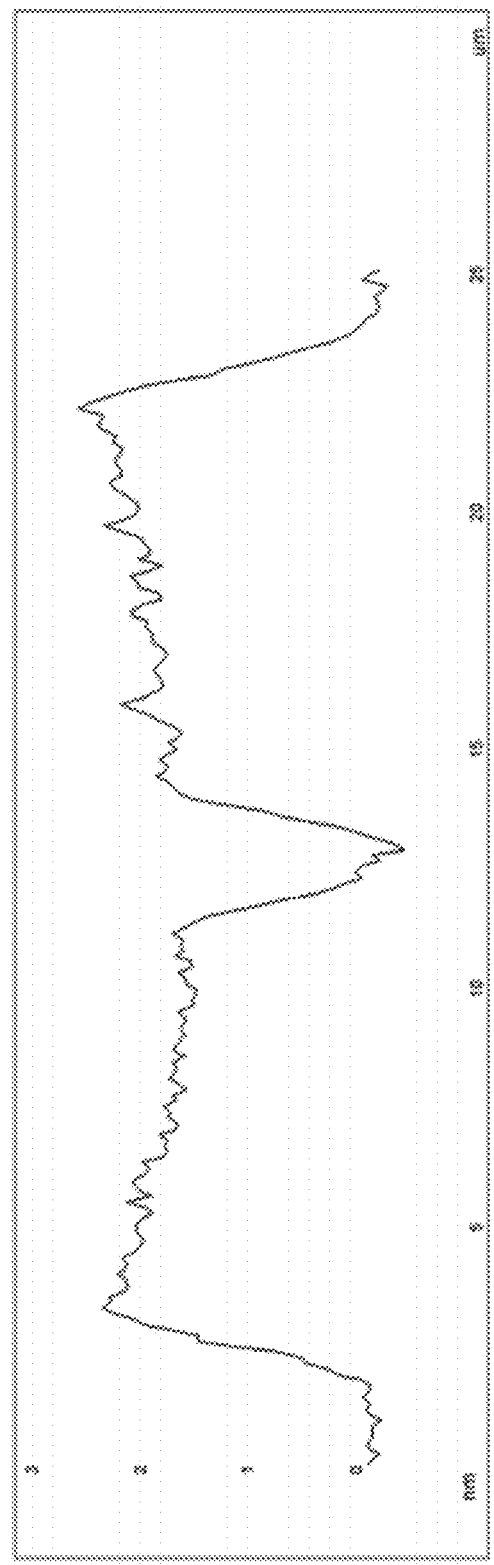
FIG. 3B is the in-line measurement results of mean height of the semi-finished biomarkers obtained from those in two regions (indicated by dashed boxes) of the microarray of FIG. 3A.

Example 2: Using AFM to Measure the Height and the Surface Morphology of the Semi-Finished Biomarkers of the Microarray to Check Surface Defects and Probe Distribution FIG. 2A is a schematic diagram of the in-line measurement results of the semi-finished biomarkers on a microarray in an experimental example of the present invention. FIG. 2B is the in-line measurement results of mean height of the semi-finished biomarkers obtained from those in two regions (indicated by dashed boxes) of the microarray of FIG. 2A. FIG. 3A is a schematic diagram of the in-line measurement results of the semi-finished biomarkers on a microarray in another experimental example of the present invention. FIG. 3B is the in-line measurement results of mean height of the semi-finished biomarkers obtained from those in two regions (indicated by dashed boxes) of the microarray of FIG. 3A.

As shown in FIG. 2A, the donut shape is shown in each one of 4 areas of the microarray and the aggregated particles is indicated by a dashed circle in the lower right area of the microarray. As shown in FIG. 2B, the donut shape indicates the height of the semi-finished biomarkers on the outside is higher than that on the inside in each one of the 4 areas, which means the quality of the biomarkers in one area is varied. In other words, the donut shape and the aggregated particles indicate the quality of the microarray is poor. On the other hand, as shown in FIGS. 3A and 3B, the surface morphology and the height of the semi-finished biomarkers of the microarray is more uniform, which means the quality of the biomarkers in one area is stable. Therefore, the quality of the microarray of FIGS. 3A and 3B is better than that of FIGS. 2A and 2B. In other words, the completeness and distribution of the semi-finished biomarkers of the microarray may be determined by the surface morphology and the height of the semi-finished biomarkers.

To sum up, the invention provides a method for in-line measurement of the quality of a microarray, which includes monitoring a semi-finished biomarker synthesized in-situ by an atomic force microscope, and determining the quality of the semi-finished biomarker based on the in-line measurement result obtained from the atomic force microscope. Accordingly, the cost of the microarray is reduced, and the accuracy, reliability and yield of the microarray are improved.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for in-line measurement of the quality of a microarray, comprising:
   providing a solid substrate, wherein the solid substrate comprises a plurality of areas in an array;
   performing an initial check step by an atomic force microscope to obtain an initial measurement result;
   in-situ synthesizing at least one biomarker on at least one of the plurality of areas by using a plurality of units through a plurality of synthesis steps, wherein after performing at least one of the plurality of synthesis step, a check step is immediately performed on a semi-product of the at least one biomarker by the atomic force microscope to obtain an in-line measurement result; and
   determining the quality of the semi-product of the at least one biomarker based on the in-line measurement result, wherein the in-line measurement result comprises a ratio of adhesion force of the semi-product of the at least one biomarker to adhesion force of the solid substrate, and when the ratio is less than 0.3, the quality of the semi-finished product meets requirements.

2. The method as claimed in claim 1, wherein the check step is performed once after performing one synthesis step.

3. The method as claimed in claim 1, wherein the check step is performed once after performing a predetermined number of synthesis steps.

4. The method as claimed in claim 1, wherein the solid substrate has a silanized surface, and the at least one biomarker is synthesized on the silanized surface.

5. The method as claimed in claim 1 further comprising forming a quality monitor key on the solid substrate, wherein the quality monitor key is used as a control for the in-line measurement result.

6. The method as claimed in claim 1 further comprising forming an overlay mark on the solid substrate.

7. The method as claimed in claim 1, wherein the in-line measurement result further comprises at least one of height, surface morphology, surface defect, roughness and density of the semi-product of the at least one biomarker.

8. The method as claimed in claim 1, wherein the biomarker comprises an oligonucleotide.

9. The method as claimed in claim 8, wherein the plurality of synthesis steps comprise a plurality of nucleotide coupling steps.

10. The method as claimed in claim 9, wherein the plurality of synthesis steps further comprise a plurality of irradiating steps.

11. The method as claimed in claim 1, wherein one of the plurality of areas of the solid substrate has a size in the nano to micron range.

12. The method as claimed in claim 1, wherein one of the plurality of areas of the solid substrate has a size less than 100 micrometers.

13. The method as claimed in claim 1, wherein the at least one biomarker on one of the plurality of areas of the solid substrate comprises at least one kind of biomarker.

14. The method as claimed in claim 1, wherein the initial measurement result comprises at least one of height, surface morphology, surface defect, roughness and adhesion force of the surface of the solid substrate.

15. The method as claimed in claim 1, wherein the surface of the solid substrate is a silanized surface.

16. The method as claimed in claim 1 further comprising comparing the initial measurement result and the in-line measurement result.

17. The method as claimed in claim 1, wherein the at least one biomarker is in-situ synthesized in multiple of the plurality of areas.

18. The method as claimed in claim 1, wherein the at least one biomarker is in-situ synthesized in multiple of the plurality of areas by the plurality of synthesis steps simultaneously.

* * * * *